US00PP31513P2

(12) United States Plant Patent
Klemm et al.

(10) Patent No.: US PP31,513 P2
(45) Date of Patent: Mar. 3, 2020

(54) POINSETTIA PLANT NAMED 'NPCW18281'

(50) Latin Name: *Euphorbia pulcherrima*
Varietal Denomination: NPCW18281

(71) Applicant: Klemm+Sohn GmbH & Co. KG, Stuttgart (DE)

(72) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/501,252

(22) Filed: Mar. 12, 2019

(51) Int. Cl.
*A01H 5/02* (2018.01)
*A01H 6/38* (2018.01)

(52) U.S. Cl.
USPC ..... Plt./306
CPC ..... *A01H 6/38* (2018.05)

(58) Field of Classification Search
USPC ..... Plt./306
CPC ..... A01H 5/02
See application file for complete search history.

*Primary Examiner* — Kent L Bell
(74) *Attorney, Agent, or Firm* — Barbara Campbell; Cochran Freund & Young LLC

(57) ABSTRACT

A new poinsettia plant particularly distinguished by having pink bracts and very good keeping quality is disclosed.

1 Drawing Sheet

Genus and species: *Euphorbia pulcherrima.*
Variety denomination: 'NPCW18281'.

BACKGROUND OF THE NEW PLANT

The present invention comprises a new and distinct variety of poinsettia, botanically known as *Euphorbia pulcherrima* and hereinafter referred to by the variety name 'NPCW18281'. 'NPCW18281' was derived from an irradiated cutting of the Poinsettia variety CHRISTMAS WISH Red, (also known as 'NPCW13218' U.S. Plant Pat. No. 26,625), having red bracts, in April 2013 in a greenhouse in Stuttgart, Germany.

In April 2014, a single plant having pink bracts was selected in Stuttgart, Germany. In February 2015, 'NPCW18281' was first asexually propagated by vegetative apical cuttings. 'NPCW18281' was found to reproduce true to type in successive generations of asexual propagation via vegetative apical cuttings in Stuttgart, Germany.

SUMMARY

The following are the most outstanding and distinguishing characteristics of this new variety when grown under normal horticultural practices in Stuttgart, Germany.

1. Pink bracts; and
2. Very good keeping quality.

DESCRIPTION OF THE PHOTOGRAPH

This new poinsettia plant is illustrated by the accompanying photograph which shows an overall view of the whole plant. The photograph is of a plant approximately 12 weeks old grown indoors in Stuttgart, Germany in December 2016. The colors shown are as true as can be reasonably obtained by conventional photographic procedures.

DESCRIPTION OF THE NEW VARIETY

The following detailed descriptions set forth the distinctive characteristics of 'NPCW18281'. The data which define these characteristics were collected from asexual reproductions carried out in Stuttgart, Germany. Data was collected on plants aged approximately 18 weeks-old after potting and grown in a glass greenhouse in Stuttgart, Germany in December 2018. Color references are to The R.H.S. Colour Chart of The Royal Horticultural Society of London (R.H.S.), 5$^{th}$ edition (2007) unless where otherwise stated.

Classification:
- *Family.*—Euphorbiaceae.
- *Species.—Euphorbia pulcherrima.*
- *Common name.*—Poinsettia.
- *Variety.*—'NPCW18281'.

Parentage: Mutation of CHRISTMAS WISH Red, (also known as 'NPCW13218' U.S. Plant Pat. No. 26,625).

Growth:
- *Blooming habit.*—Intermittent.
- *Flowering response time.*—Approximately 53 days.
- *Keeping quality.*—Very good.

Plant description:
- *Form.*—Triangular.
- *Growth habit.*—Upright.
- *Height.*—28.0 cm to 30.0 cm.
- *Width.*—25.0 cm to 30.0 cm.
- *Average number of inflorescences per plant.*—5 to 6.

Propagation:
- *Type cuttings.*—Apical cuttings.
- *Time to produce a rooted cutting.*—4 weeks.
- *Rooting habit and root color.*—Freely branching and white.

Lateral branches:
- *Color.*—RHS 143A.
- *Length.*—25.0 cm.
- *Internode length.*—1.2 cm to 3.5 cm.
- *Diameter.*—0.5 cm to 0.8 cm.
- *Branching habit.*—Freely branching.
- *Number of lateral branches per plant.*—5 to 6.
- *Texture.*—Smooth.
- *Strength.*—Medium.

Leaves:

*Quantity.*—6 to 7 per lateral branch.

*Arrangement.*—Alternate.

*Number of lobes on the leaf blade.*—1 to 3.

*Lobation depth.*—Shallow.

*Depth of the deepest sinus of the leaf blade.*—0.3 cm.

*Shape.*—Ovate.

*Apex.*—Acute.

*Base.*—Obtuse.

*Margin.*—Mostly entire.

*Length.*—8.0 cm to 14.0 cm.

*Width.*—6.0 cm to 9.0 cm.

*Texture (both surfaces).*—Smooth.

*Vein color.*—Upper surface: Transparent. Lower surface: RHS 139D.

*Venation pattern.*—Reticulate.

*Variegation.*—Absent.

*Color.*—Mature foliage: Upper surface: RHS 139A. Lower surface: RHS 138B. Immature foliage: Upper surface: RHS 143A. Lower surface: RHS 138B.

*Leaf petiole.*—Length: 3.0 cm to 6.0 cm. Diameter: 0.2 cm to 0.3 cm. Color: Upper (part) surface: RHS 181A. Lower (part) surface: RHS 138C. Texture: Smooth. Strength: Medium.

Inflorescence:

*Type and habit.*—Cluster of cyathia.

*Quantity per lateral branch.*—1 compound of cyathias accompanied by bracts.

*Position relative to foliar plane.*—Above.

*Lastingness of inflorescence on the plant.*—4 weeks.

*Natural flowering season.*—Mid November.

*Diameter.*—26.0 cm to 29.0 cm.

*Height.*—3.0 cm to 4.0 cm.

*Fragrance.*—Absent.

Bracts:

*Number of bracts per inflorescence.*—6 to 9.

*Shape.*—Ovate.

*Apex.*—Acute.

*Base.*—Obtuse.

*Margin.*—Mostly entire, older bracts are slightly serrate.

*Size.*—Length: 9.0 cm to 11.0 cm. Width: 4.0 cm to 8.0 cm.

*Texture (both upper and lower surfaces).*—Smooth.

*Venation pattern.*—Reticulate.

*Vein color.*—Upper surface: RHS 138B. Lower surface: RHS 138B.

*Bract color.*—Upper surface: Close to RHS 47D. Lower surface: Close to RHS 48B.

*Bract petiole.*—Length: 0.5 cm to 2.5 cm. Diameter: 0.2 cm to 0.3 cm. Color: Upper (part) surface: RHS 58A. Lower (part) surface: RHS 181C. Texture: Smooth. Strength: Medium.

Cyme:

*Diameter.*—1.0 cm to 2.5 cm.

*Cyathia number.*—7 to 10 per inflorescence.

*Deformation of glands of the cyathium.*—Absent.

*Timing of opening of cyathia.*—End of November. First pollen appears in parallel to opening of the nectar cups; stigmas appear 1 to 2 weeks later.

*Cyathium.*—Shape: Ovate. Texture (inner and outer surfaces): Smooth. Diameter: 0.2 cm to 0.6 cm. Length: 0.3 cm to 0.8 cm. Color: RHS 143C (main color).

*Peduncle.*—Color: RHS 142B. Length: 0.2 cm to 0.3 cm. Diameter: 0.1 cm. Texture: Smooth. Strength: Medium.

*Nectar cups.*—Number: 1 per cyathium. Diameter: 0.1 cm. Length: 0.4 cm to 0.5 cm. Color: RHS 13B in center to orange red on side; immature colored RHS 138D. Shape: Lip-shaped. Texture (inner and outer surfaces): Smooth.

Reproductive organs:

*Stamen quantity.*—5 to 10 per cyathium.

*Stamen shape.*—Ovate.

*Filament length.*—0.25 cm.

*Filament color.*—RHS 46A.

*Pollen quantity.*—Moderate.

*Pollen color.*—RHS 12A.

*Gynoecium.*—Present. Pistil quantity per cyathium: 1. Pistil length: 0.2 cm. Stigma form: Divided in 2 parts. Stigma color: RHS 183A. Style length: 0.2 cm. Style color: RHS 183A. Ovary length: 0.05 cm. Ovary color: RHS 143C.

Fruit and seed set: None observed.

Disease and pest resistance: No special disease or pest resistance observed.

COMPARISON WITH PARENTAL AND KNOWN VARIETY

'NPCW18281' is a distinct variety of poinsettia. 'NPCW18281' differs from the parental line CHRISTMAS WISH Red in that CHRISTMAS WISH Red has red bracts colored RHS 46B whereas 'NPCW18281' has pink bracts colored close to RHS 47D.

'NPCW18281' is distinguished from commercial line CHRISTMAS BEAUTY Pink (also known as 'NPCW11203', unpatented) in that 'NPCW18281' has medium to large bracts and a flowering response time of approximately 53 days whereas CHRISTMAS BEAUTY Pink has small to medium bracts and a flowering response time of approximately 56 days.

We claim:

1. A new and distinct variety of poinsettia plant designated 'NPCW18281' as illustrated and described herein.

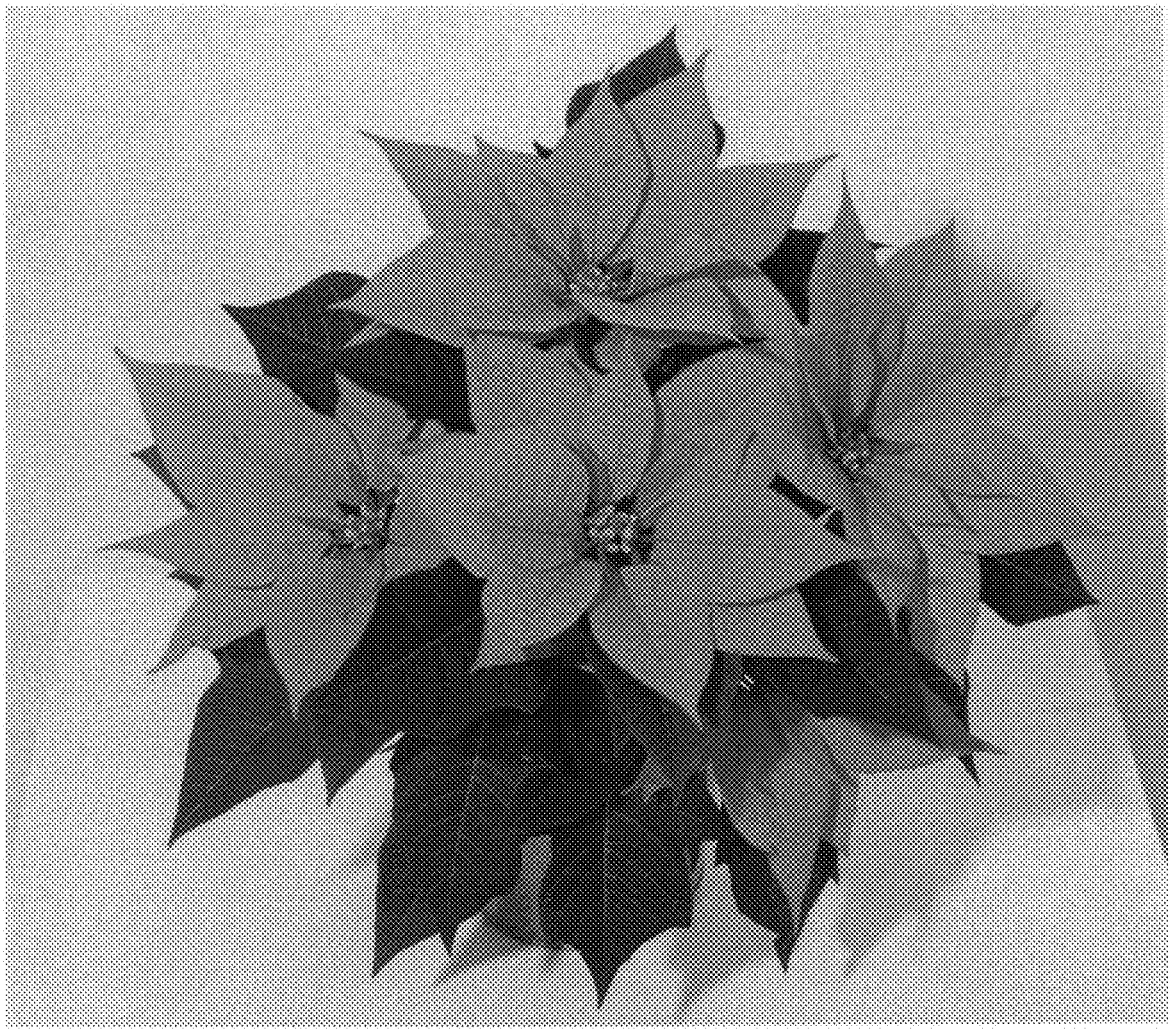

* * * * *